(12) United States Patent
Creel et al.

(10) Patent No.: US 12,095,903 B2
(45) Date of Patent: *Sep. 17, 2024

(54) METHODS FOR DISSEMINATING REASONING SUPPORTING INSIGHTS WITHOUT DISCLOSING UNIQUELY IDENTIFIABLE DATA, AND SYSTEMS FOR THE SAME

(71) Applicant: COTIVITY CORPORATION, Wilton, CT (US)

(72) Inventors: Christopher Taylor Creel, Atlanta, GA (US); William Paige Vestal, Milton, GA (US); Christopher Shawn Watson, Alpharetta, GA (US)

(73) Assignee: COTIVITI, INC., Atlanta, GA (US)

( * ) Notice: Subject to any disclaimer, the term of this patent is extended or adjusted under 35 U.S.C. 154(b) by 637 days.

This patent is subject to a terminal disclaimer.

(21) Appl. No.: 17/605,559

(22) PCT Filed: May 17, 2018

(86) PCT No.: PCT/US2018/033194
§ 371 (c)(1),
(2) Date: Oct. 21, 2021

(87) PCT Pub. No.: WO2018/222406
PCT Pub. Date: Dec. 6, 2018

(65) Prior Publication Data
US 2022/0123926 A1 Apr. 21, 2022

Related U.S. Application Data
(63) Continuation of application No. 15/610,945, filed on Jun. 1, 2017, now Pat. No. 10,958,422.

(51) Int. Cl.
*H04L 9/08* (2006.01)
*G06N 5/022* (2023.01)

(52) U.S. Cl.
CPC .......... *H04L 9/0825* (2013.01); *G06N 5/022* (2013.01)

(58) Field of Classification Search
CPC .............................. G06N 5/02; H04L 9/0825
See application file for complete search history.

(56) References Cited

U.S. PATENT DOCUMENTS

| | | | |
|---|---|---|---|
| 5,343,554 A | 8/1994 | Koza et al. | |
| 5,602,933 A * | 2/1997 | Blackwell | H04N 1/32101 902/4 |
| 5,778,157 A | 7/1998 | Oatman et al. | |
| 6,813,615 B1 | 11/2004 | Colasanti et al. | |

(Continued)

FOREIGN PATENT DOCUMENTS

WO   2017078548 A1   5/2017

OTHER PUBLICATIONS

International Search Report and Written Opinion from International Application No. PCT/US2020/017424 mailed Apr. 30, 2020, pp. 1-16.

(Continued)

*Primary Examiner* — Paulinho E Smith
(74) *Attorney, Agent, or Firm* — Perkins Coie LLP (57) ABSTRACT

Embodiments disclosed herein relate to methods and systems for disseminating reasoning supporting insights made with uniquely identifiable data without disclosing the uniquely identifiable data.

20 Claims, 6 Drawing Sheets

(56) References Cited

U.S. PATENT DOCUMENTS

| | | | | |
|---|---|---|---|---|
| 7,216,088 | B1* | 5/2007 | Chappel | G06Q 10/063118 |
| | | | | 705/7.17 |
| 7,917,455 | B1* | 3/2011 | Dobson | G06N 20/00 |
| | | | | 706/12 |
| 8,752,648 | B2* | 6/2014 | Goebel | G06F 18/254 |
| | | | | 702/9 |
| 8,762,142 | B2* | 6/2014 | Jeong | G10L 15/16 |
| | | | | 704/203 |
| 8,838,446 | B2* | 9/2014 | Jeong | G10L 15/02 |
| | | | | 704/232 |
| 9,053,436 | B2* | 6/2015 | Dalessandro | G06N 5/022 |
| 9,111,228 | B2* | 8/2015 | Collica | G06N 7/01 |
| 2003/0101089 | A1* | 5/2003 | Chappel | G06Q 10/06313 |
| | | | | 705/7.17 |
| 2003/0135453 | A1 | 7/2003 | Caulfield et al. | |
| 2004/0093315 | A1* | 5/2004 | Carney | G06N 3/08 |
| | | | | 706/15 |
| 2005/0283429 | A1* | 12/2005 | Bates | G06Q 40/03 |
| | | | | 705/38 |
| 2007/0011114 | A1* | 1/2007 | Chen | G06N 3/086 |
| | | | | 706/15 |
| 2007/0179966 | A1 | 8/2007 | Li et al. | |
| 2008/0005628 | A1 | 1/2008 | Underdal et al. | |
| 2008/0294644 | A1 | 11/2008 | Liu et al. | |
| 2009/0010495 | A1* | 1/2009 | Schamp | G06F 18/254 |
| | | | | 382/106 |
| 2010/0004957 | A1* | 1/2010 | Ball | G06Q 40/00 |
| | | | | 705/35 |
| 2010/0031000 | A1 | 2/2010 | Flynn et al. | |
| 2010/0306167 | A1* | 12/2010 | Crawford | G06F 16/904 |
| | | | | 706/60 |
| 2011/0030057 | A1* | 2/2011 | Chen | H04L 63/1416 |
| | | | | 726/25 |
| 2011/0213981 | A1* | 9/2011 | Griffin | H04L 9/3231 |
| | | | | 713/172 |
| 2011/0307435 | A1 | 12/2011 | Overell et al. | |
| 2013/0117280 | A1* | 5/2013 | Donaldson | G06F 16/17 |
| | | | | 707/754 |
| 2014/0108321 | A1 | 4/2014 | Buchanan et al. | |
| 2015/0100295 | A1* | 4/2015 | Jetcheva | G06F 30/367 |
| | | | | 703/18 |
| 2015/0227741 | A1* | 8/2015 | Permeh | G06F 21/51 |
| | | | | 726/22 |
| 2016/0012314 | A1* | 1/2016 | Ramamurthy | G06V 10/7715 |
| | | | | 382/160 |
| 2016/0156595 | A1 | 6/2016 | Wu et al. | |
| 2016/0210502 | A1* | 7/2016 | Xu | G06V 40/20 |
| 2016/0247061 | A1* | 8/2016 | Trask | G06N 3/04 |
| 2016/0350389 | A1 | 12/2016 | Kloke et al. | |
| 2017/0083637 | A1 | 3/2017 | Cho et al. | |
| 2017/0132217 | A1* | 5/2017 | Na | G06N 3/044 |
| 2017/0220698 | A1 | 8/2017 | Dietrich et al. | |
| 2017/0270910 | A1* | 9/2017 | Jung | G06N 3/04 |
| 2018/0052828 | A1* | 2/2018 | Na | G06F 40/58 |
| 2018/0121622 | A1* | 5/2018 | Armstrong | G06N 5/01 |
| 2018/0129325 | A1* | 5/2018 | Shreve | G06Q 40/03 |
| 2018/0174044 | A1* | 6/2018 | Na | G06N 3/08 |
| 2018/0336487 | A1* | 11/2018 | Moore | G06N 20/20 |
| 2018/0349773 | A1* | 12/2018 | Creel | G06N 5/01 |
| 2019/0051292 | A1* | 2/2019 | Na | G06N 3/045 |
| 2019/0155909 | A1* | 5/2019 | Na | G06F 40/58 |
| 2019/0303760 | A1* | 10/2019 | Kumar | G06N 3/126 |
| 2019/0370662 | A1* | 12/2019 | Song | G06N 3/088 |
| 2019/0377819 | A1* | 12/2019 | Filliben | G06N 3/084 |
| 2019/0378049 | A1* | 12/2019 | Widmann | G06Q 20/4016 |
| 2020/0025935 | A1* | 1/2020 | Liang | G06V 20/64 |
| 2020/0034666 | A1* | 1/2020 | Yun | G06F 18/214 |
| 2020/0073948 | A1* | 3/2020 | Lee | G06F 40/289 |
| 2020/0080843 | A1* | 3/2020 | Chowdhary | G01C 19/32 |

OTHER PUBLICATIONS

International Search Report and Written Opinion from International Application No. PCT/US2018/033194 mailed Aug. 8, 2018, pp. 1-15.

International Search Report and Written Opinion from International Application No. PCT/US2018/054367 mailed Dec. 3, 2018, pp. 1-14.

Peng, et al., "Cross-media analysis and reasoning: advances and directions", In: Frontiers of Information Technology & Electronic Engineering, Jan. 1, 2017, pp. 1-14. https://link.springer.com/content/pdf/10.1631/FITEE.1601787.PDF.

U.S. Appl. No. 15/610,945, filed Jun. 1, 2017, pp. 1-56.

Communication pursuant to Article 94(3) EPC mailed Feb. 2, 2024 for European Patent Application No. 18809974.1 (5 pages).

Communication pursuant to Article 94(3) EPC mailed Jul. 22, 2022 for European Patent Application No. 18809974.1 (5 pages).

* cited by examiner

| | |
|---|---|
| TRUE | This a new claim |
| TRUE | There are two claims lines with the same date of service |
| TRUE | The same two claims lines have the same procedure code |
| TRUE | The same two claims lines have the same number of units |
| TRUE | The claim lines come from the same form type |
| FALSE | The claim under evaluation is a F-1450 |
| TRUE | The two claim lines have the same place of service |
| FALSE | The claim line under evaluation has zero modifier |
| TRUE | The claim line under evaluation has one modifiers |
| FALSE | The other claim line has zero modifiers |
| TRUE | The other claim line has one modifiers |
| FALSE | The modifiers for both claim lines are the same |
| TRUE | The modifiers for the claim line under evaluation bounce off the modifiers in the other claim line |
| TRUE | The modifiers of the other claim line do not contain exception modifiers for the claim line under evaluation |
| INSIGHT | Deny the claim under evaluation as duplicate |

FIG. 6

METHODS FOR DISSEMINATING REASONING SUPPORTING INSIGHTS WITHOUT DISCLOSING UNIQUELY IDENTIFIABLE DATA, AND SYSTEMS FOR THE SAME

CROSS-REFERENCE TO RELATED APPLICATIONS

This patent document is a national phase application of and claims priority to International Application No. PCT/US2018/033194, titled "METHODS FOR DISSEMINATING REASONING SUPPORTING INSIGHTS WITHOUT DISCLOSING UNIQUELY IDENTIFIABLE DATA, AND SYSTEMS FOR THE SAME", filed May 17, 2018, which claims priority to U.S. patent application Ser. No. 15/610,945 filed on 1 Jun. 2017, issued as U.S. Pat. No. 10,958,422, on 23 Mar. 2021, the disclosure of which is incorporated herein, in its entirety, by this reference.

BACKGROUND

Uniquely identifiable data or information is data or information that is attributable to specific individuals, companies, or other entities. Uniquely identifiable data can include individually identifiable data, personally identifiable information, protected health information, etc. Handling uniquely identifiable data, such as storing, using, or generating such data presents many challenges and is regulated by law in many instances. For example, personal health information is regulated in the U.S. by the Health Insurance Portability and Accountability Act (HIPAA) regulations and the HITECH Act, among others. These regulations require stringent controls and security measures to prevent unwanted disclosure of such uniquely identifiable data.

Entities that handle uniquely identifiable data typically have policies about how such data is secured, used, and disseminated. However, use of uniquely identifiable data typically requires human interaction with said data, which creates opportunities for unwanted disclosure of said data.

SUMMARY

Embodiments disclosed herein relate to methods and systems for determining insights using uniquely identifiable data and disseminating the rationale for the insights without disclosing the uniquely identifiable data. In an embodiment, a method of explaining insight reasoning about uniquely identifiable data over a computer network without exposing the uniquely identifiable data to one or more employees of a hosting entity is disclosed. The method includes, with a computing device, automatically determining an insight using uniquely identifiable data attributable to a unique entity and a reasoning graph. The reasoning graph includes a plurality of leaf nodes each of which provide an insight identified by an insight identifier. The reasoning graph further includes a plurality of reasoning paths each of which terminate in one of the plurality of leaf nodes. The reasoning graph also includes a plurality of reasoning functions each of which defines criteria for making a discrete decision made with the uniquely identifiable data at a point along a reasoning path. The reasoning path to a specific insight is defined at the leaf node by the insight identifier and includes only the reasoning functions and the discrete decisions in the reasoning path. The method further includes, responsive to determining the insight and with the computing device, providing a universally unique identifier (UUID) encoding the insight identifier. The method also includes providing a portal associated with the insight identifier, the portal configured receive input of the UUID and to display each of the plurality of reasoning functions and the discrete decisions from the reasoning path corresponding to the insight identifier encoded in the UUID. The method includes responsive to input of the UUID, displaying, in the portal, each of the plurality of reasoning functions and the discrete decisions made using the uniquely identifiable data along the reasoning path corresponding to the insight identifier.

In an embodiment, a system for providing de-identified insight information is disclosed. The system includes a server including at least one memory storage medium having an encrypted database storing uniquely identifiable data attributable a unique entity and a plurality of reasoning graphs therein. Each of the plurality of reasoning graphs includes a plurality of leaf nodes each of which provide an insight identified by an insight identifier. Each of the plurality of reasoning graphs further includes a plurality of reasoning paths each of which terminate in one of the plurality of leaf nodes, Each of the plurality of reasoning graphs also includes a plurality of reasoning functions each of which defines criteria for making a discrete decision with the uniquely identifiable data at a point along a reasoning path. The reasoning path to a specific insight is defined at the leaf node by the insight identifier and includes only the reasoning functions and the discrete decisions in the reasoning path. The server further includes at least one processor operably coupled to the memory storage medium. The at least one processor is configured to automatically determine the insight using uniquely identifiable data attributable to the unique entity and one the plurality of reasoning graphs. The at least one processor of the server is configured to produce a UUID encoding the insight identifier. The at least one processor of the server is configured to output the UUID. The at least one processor is further configured to provide a portal associated with the insight identifier. The at least one processor is configured to receive the UUID as input via the portal. The at least one processor is also configured to display, in the portal, each of the plurality of reasoning functions and the discrete decisions made using the uniquely identifiable data along the reasoning path corresponding to the insight identifier, responsive to receiving the UUID.

Features from any of the disclosed embodiments may be used in combination with one another, without limitation. In addition, other features and advantages of the present disclosure will become apparent to those of ordinary skill in the art through consideration of the following detailed description and the accompanying drawings.

BRIEF DESCRIPTION OF THE DRAWINGS

The drawings illustrate several embodiments of the invention, wherein identical reference numerals refer to identical or similar elements or features in different views or embodiments shown in the drawings.

DETAILED DESCRIPTION

Embodiments disclosed herein relate to methods and systems for disseminating reasoning supporting insights made with uniquely identifiable data without disclosing the uniquely identifiable data. Uniquely identifiable data or information can include individually identifiable data or information, personally identifiable information, protected health information, personally identifiable financial information, or any other data or information that is capable of, or can be used in, identifying an individual. Uniquely identifiable data provides details about an individual or unique entity that may be useful to make one or more insights (e.g., decisions or conclusions) related to the individual or unique entity. For example, uniquely identifiable data is useful for making a myriad of informed decisions or insights such as health related insights (e.g., insurance coverage, the propriety of medical procedures, the propriety of medications, etc.), financially related insights (e.g., qualification for a mortgage or loan, propriety of rate adjustments, etc.), insurance related insights (e.g., propriety of coverage of a claim, rate decisions, qualifications for enrollment, etc.), or other insights such as a determination of likely perpetration of fraud. An insight may include a decision or an outcome of a series of queries based on one or more policies. For example, an insight may include a determination or conclusion that an outcome falls within a set of coverage criteria; a determination that the outcome falls outside of the set of coverage criteria; a determination that a healthcare related expense will or will not be covered; a determination that the individual should or should not receive the selected procedure; a determination that the individual should or should not receive a selected medication; a determination that a medical professional is committing fraud or malpractice; a determination that the individual is committing fraud, a determination that a unique entity should or should not receive financial assistance (e.g., a loan, a grant, etc.); or a determination that unique entity does or does not qualify for an economic benefit (e.g., tax exemption, charitable status, etc.).

However, using and possessing uniquely identifiable data comes at great costs to a hosting entity, which may include infrastructure to protect against unwanted disclosure of the uniquely identifiable data/information and sequestration of one or more employees with access to the uniquely identifiable data. Such infrastructure can include computer systems architecture and policies to limit or prevent disclosure of uniquely identifiable data. A hosting entity may include a data processing center or provider that receives policies and uniquely identifiable data and determines insights with respect to the policies using the uniquely identifiable data. The hosting entity may provide computing services, such as computational expertise and bandwidth as well data storage and processing (e.g., provide secure storage and handling of uniquely identifiable data). An even greater challenge is presented when communication of insights related to uniquely identified information are sent outside of the hosting entity that uses the uniquely identifiable data to make the insight. For example, once the hosting entity (e.g., insurer, service provider, organization, business, etc.) determines that a medical procedure should not be covered by insurance, the hosting entity may communicate this information to the medical services provider, the insured, the insurer, or another entity. However, such communication risks disclosing uniquely identifiable data about the insured, the insurer, or the medical services provider.

The embodiments of methods and systems disclosed herein utilize reasoning graphs to determine an insight. The reasoning graphs include a plurality of reasoning functions which query uniquely identifiable data, along a reasoning path through the reasoning graph, to arrive at an insight at a terminal leaf node in the reasoning graph. The reasoning graphs may apply to many individual's or entity's uniquely identifiable data and therefore provide a many-to-one correlation therebetween. In such embodiments, no direct one-to-one correlation between an individual/entity and the reasoning path may be made by disclosing a reasoning path through the reasoning graph to the insight. Accordingly, the methods and systems herein are directed to improvements to data protection and encryption of uniquely identifiable data and insights based on the same.

Embodiments disclosed herein are directed to methods and systems for disseminating reasoning supporting insights made with uniquely identifiable data without disclosing the uniquely identifiable data. The methods and system disclosed herein include making such insights with uniquely identifiable data in a systematic way and in a secure manner, without exposing uniquely identifiable data to any entity, even the employees of the hosting entity (e.g., insight or decision-making entity).

Figure 1:
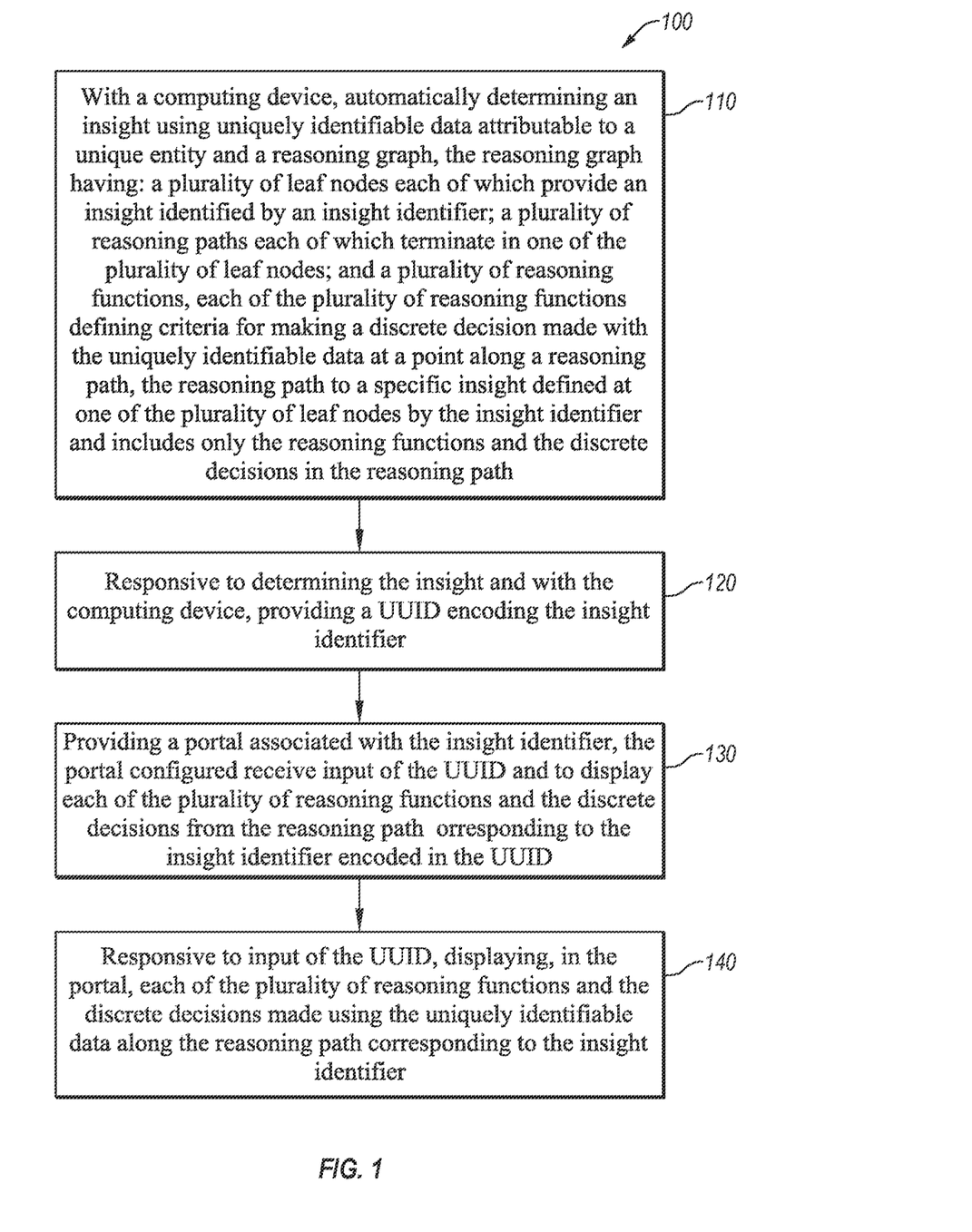
FIG. 1 is a flow chart of a method of explaining insight reasoning about uniquely identifiable data over a computer network without exposing the uniquely identifiable data, according to an embodiment.

FIG. 1 is a flow chart of a method 100 of explaining insight reasoning about uniquely identifiable data over a computer network without exposing the uniquely identifiable data, according to an embodiment. The method 100 is useful for explaining insight reasoning about uniquely identifiable data over a computer network without exposing the uniquely identifiable data to employees of a hosting entity. The method 100 includes an act 110 of, with a computing device, automatically determining an insight using uniquely identifiable data attributable to a unique entity and a reasoning graph. The reasoning graph includes a plurality of leaf nodes each of which provide an insight identified by an insight identifier (ID), a plurality of reasoning paths each of which terminate in one of the plurality of leaf nodes, and a plurality of reasoning functions. Each of the plurality of reasoning functions defines criteria for making a discrete decision made with the uniquely identifiable data at a point along a reasoning path. The reasoning path to a specific insight is defined at the leaf node by the insight ID and includes only reasoning functions and discrete decisions in the reasoning path. Because uniquely identifiable data from many different individuals can travel down the same reasoning path, disclosing only the insight, reasoning path, and discrete decisions therealong breaks any possible one-to-one relationship between the reasoning path and the uniquely identifiable data. Accordingly, the insight and reasoning path can be disclosed without disclosing the uniquely identifiable data used to arrive at the insight.

The method 100 further includes an act 120 of responsive to determining the insight and with the computing device, providing a UUID encoding the insight ID. The method 100 also includes an act 130 of providing a portal associated with the insight ID. The portal is configured receive input of the UUID and to display each of the plurality of reasoning functions and discrete decisions from the reasoning path corresponding to the insight ID encoded in the UUID. The method 100 additionally includes an act 140 of responsive to input of the UUID, displaying, in the portal, each of the plurality of reasoning functions and the discrete decisions made using the uniquely identifiable data along the reasoning path corresponding to the insight ID.

The act 110 of automatically determining an insight using uniquely identifiable data attributable to a unique entity and a reasoning graph, with a computing device, can include using any reasoning graph, such as an acyclic, directed reasoning graph (e.g., directed, binary decision tree) to determine an insight. Acyclic, directed reasoning graphs have only one direction of flow and do not result in logic loops. Additionally, acyclic, directed reasoning graphs may include a plurality of insights each located at one of a plurality of leaf nodes in the graph. Each of the leaf nodes or insights represents a terminal node in the reasoning graph. Each of the insights may be reached from an initial point via a discrete reasoning path through the reasoning graph. Thus, the outcome of the reasoning graph may include only one insight from among the plurality of insights and/or only one reasoning path from among the plurality of reasoning paths. In some embodiments, the reasoning graph and any portions thereof may be presented in computer readable and executable code.

The computing device may include one or more of computer(s), server(s), or computer network(s). The computing device may include one or more operational programs stored therein. The one or more operational programs may be adapted to cause the computing device (e.g., via a processor therein) to determine an insight using a reasoning graph stored therein by answering queries in the reasoning functions of the reasoning graph with the uniquely identifiable data. The computing device or a portion thereof (e.g., server(s)) may be configured to store and access the uniquely identifiable data without relaying the same to any other portions of the computing device (e.g., outside of the server(s)) or entities. The computing device may be used to determine an insight with a selected reasoning graph associated with a selected unique entity.

Unique entities may include an individual person (e.g., patient, insured, suspect, client, applicant, etc.), a company (e.g., insurer, services provider, or government entity), financial institution, hosting entity, or any other entity which may have uniquely identifiable data attributable thereto that is used to determine an insight. For example, the unique entity may include an individual seeking healthcare and the uniquely identifiable data may include protected health information of the individual. In some embodiments, the unique entity may include a medical services provider (e.g., doctor or hospital) and the uniquely identifiable data may include personal health information or financial information of a patient. In some embodiments, the unique entity may include a financial services provider (e.g., a bank) and the uniquely identifiable data may include personal financial information of an applicant for a loan.

In some embodiments, the reasoning graph(s) includes a plurality of reasoning functions each defining a fork in the reasoning graph. Each of the plurality of reasoning functions defines criteria for making a discrete decision (made using at least some of the uniquely identifiable data) at a respective fork in the reasoning graph (e.g., a point along a reasoning path). Each of the reasoning functions may direct a reasoning path in a selected to direction through the reasoning graph to arrive at an insight at a respective leaf node. Accordingly, the reasoning path includes only those reasoning functions and discrete decisions used in determining the insight (e.g., arriving at the leaf node). The reasoning path may include discrete portions including a reasoning function and a discrete decision based on the reasoning function. The discrete portions may also include insights. The reasoning graph(s) may include a plurality of reasoning paths each of which include a plurality of reasoning functions and terminate in one of the plurality of leaf nodes. The leaf node is a terminal node in a machine readable and executable version of the reasoning graph. The insight is identified at the leaf node by an insight identifier (insight ID). The insight ID may encode the reasoning path. The reasoning path to a specific insight at a specific leaf node may be unique and, therefore, may have a unique insight ID provided at the leaf node. For example, in acyclic, directed graphs, each insight or leaf node can be reached by only a single reasoning path, which can be identified by the insight ID.

As the processing of uniquely identifiable data using a reasoning graph is accomplished via a computer readable and executable program, the reasoning path can be identified at the leaf node by an insight ID. The insight ID may encode each reasoning function and discrete decision (e.g., decision based on the reasoning function and uniquely identifiable data) corresponding to the reasoning path. Accordingly, the insight ID and reasoning path can identify each query, criteria, and outcome (e.g., decision based on the query, criteria, and uniquely identifiable data) used to arrive at the insight. The uniquely identifiable data can be divorced from the query, criteria, and outcome to provide a de-identified or otherwise non-identifiable information source for entities associated with the insight. For example, the reasoning path to a specific insight may be defined at the leaf node by the insight ID and may include only reasoning functions and discrete decisions in the reasoning path, not the uniquely identifiable data from which the discrete decisions are made. Uniquely identifiable data from any of a number of individuals or entities may travel along the same reasoning path, and therefore may not directly correlate to a specific individual, thereby breaking any possible one-to-one connection between a reasoning graph or any portions thereof to the specific individual. Accordingly, the reasoning graphs, reasoning paths, reasoning functions, discrete decisions, and insights may be disclosed without disclosing uniquely identifiable data.

Reasoning graphs may have any number of reasoning functions and/or insights therein, such as at least 2 reasoning functions and at least 3 insights. For example, a reasoning graph may include about 2 reasoning functions to about 1000 reasoning functions, such as 3 to 100, 5 to 50, 2 to 20, 10 to 100, 20 to 100, less than 100, less than 50, or less than 20 reasoning functions. In some embodiments, a reasoning graph may include any number of insights, such as 2 insights to about 1000 insights, such as 3 to 100, 5 to 50, 2 to 20, 10 to 100, 20 to 100, less than 100, less than 50, or less than 20 insights. In some embodiments, the number of possible insights on a reasoning graph may be n+1, where n is the number of reasoning functions.

Reasoning functions may include a query and criteria for determining an outcome of the query, such as a threshold value or a binary absence or presence of a condition. Accordingly, the outcomes of reasoning functions can be based on qualitative and/or quantitative criteria. For example, a query of a reasoning function may set a threshold level of the number of times an individual has been prescribed a certain medication, and uniquely identifiable data corresponding to an individual who has submitted a claim for said medication may be in excess of the threshold level. The discrete decision associated with the threshold value of the reasoning function may dictate that next steps in the reasoning path travel through one or more reasoning functions designed to determine if the individual may be better served by a different treatment, should be covered under a policy, or is obtaining an amount of medication that is indicative of addiction or fraud.

Each reasoning function can be written (e.g., encoded into a machine readable and executable program) according to a policy. Policies can include one or more of governmental instructions or recommendations, such as FDA recommendations, FHA guidelines, or state or federal statutes; professional guides such as the pharmaceutical compendia, procedures manuals for medical practices, underwriting guide books; or internal criteria, such as underwriting polices or accounting policies or targets. The reasoning functions can each be written to incorporate different criteria of a policy in queries directed to determining if a particular insight is applicable to the uniquely identifiable data (e.g., a particular action should or should not be taken). The cumulative outcomes or discrete decisions of the reasoning functions in each reasoning path define how or which insight is reached. Each reasoning function informs a subsequent reasoning function and the eventual insight. Each reasoning function queries some portions of a larger question that is answered at an insight. For example, the insight may include a healthcare related outcome and each of the reasoning functions may include a healthcare-related query and/or decision, such as, was the patient diagnosed with a condition associated with a prescribed medication.

As noted above, an insight may include a final determination or conclusion that: an outcome falls within a set of coverage criteria, the outcome falls outside of the set of coverage criteria, a healthcare-related expense will or will not be covered, the individual should or should not receive the selected procedure, the individual should or should not receive a selected medication; a medical professional is committing fraud or malpractice, the individual is committing fraud, a unique entity should or should not receive financial assistance (e.g., a loan, a grant, etc.), the unique entity does or does not qualify for an economic benefit (e.g., tax exemption, charitable status, etc.), or any other determination or conclusion.

In some embodiments, the uniquely identifiable data may include only those pieces of information that relate to the respective insight. In some embodiments, the insight includes a final determination or conclusion about the propriety of a decision associated with the uniquely identifiable data. For example, the uniquely identifiable data or information attributable to the unique entity may include protected health information and the insight may include a determination of propriety of a decision associated therewith, such as propriety of a recommended procedure or medication, or interest amount on a loan. The hosting entity may include an insurer or a service provider and the uniquely identifiable data may identify one or more of an insured individual or a medical professional associated therewith.

Figure 2:
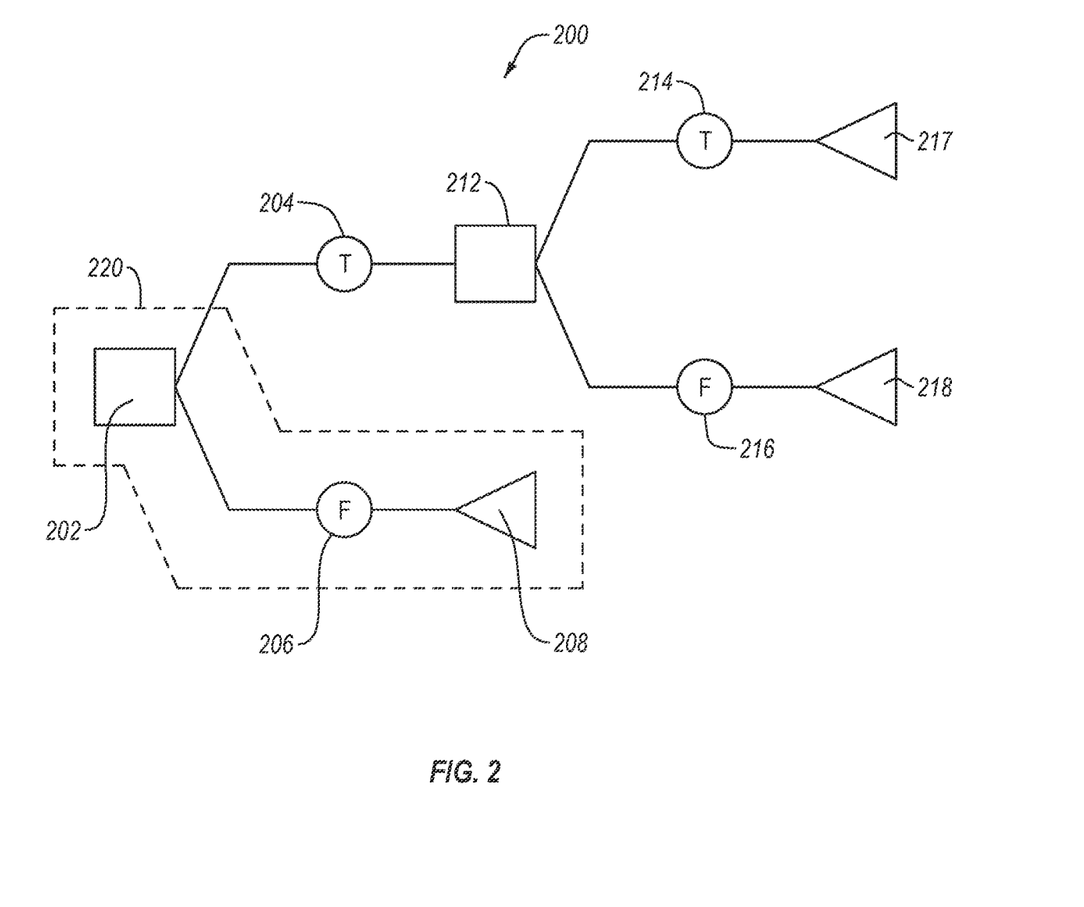
FIG. 2 is a schematic of a reasoning graph, according to an embodiment.
Figure 3:
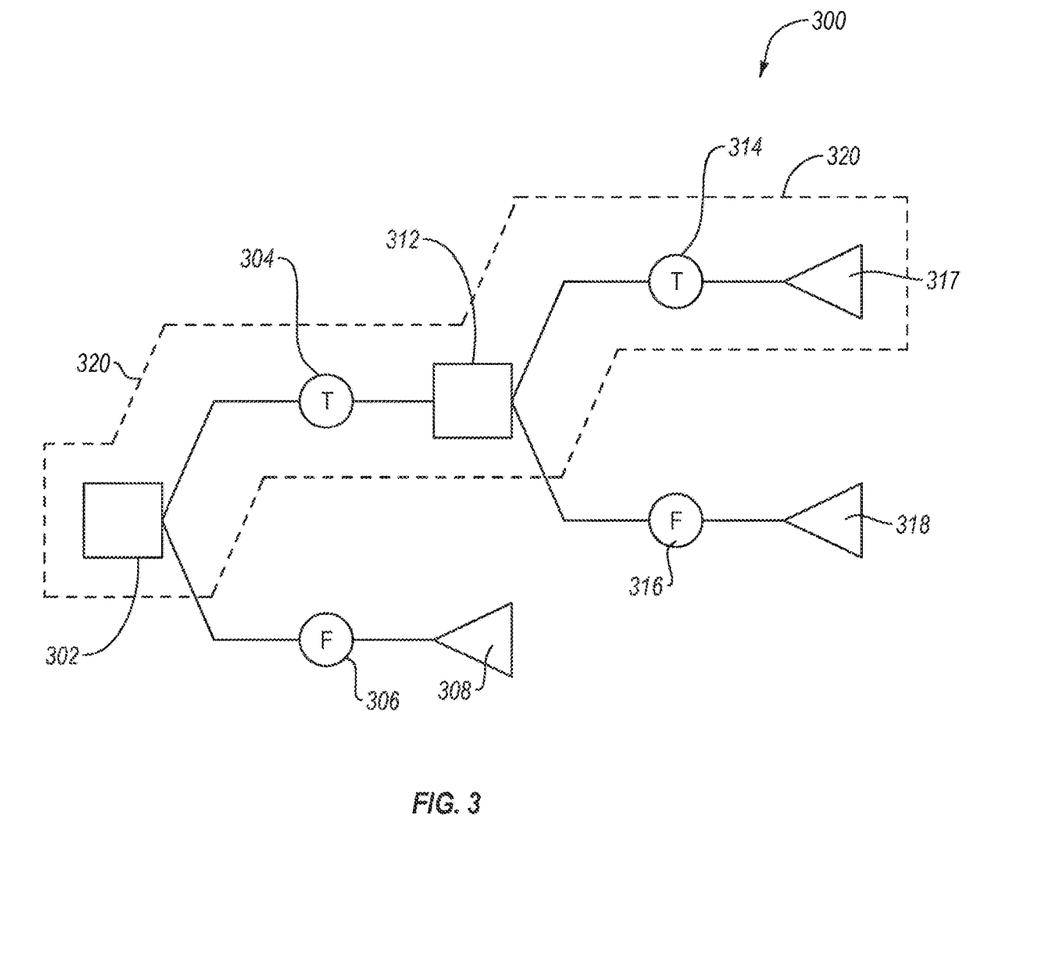
FIG. 3 is a schematic of a reasoning graph, according to an embodiment.
Figure 4:
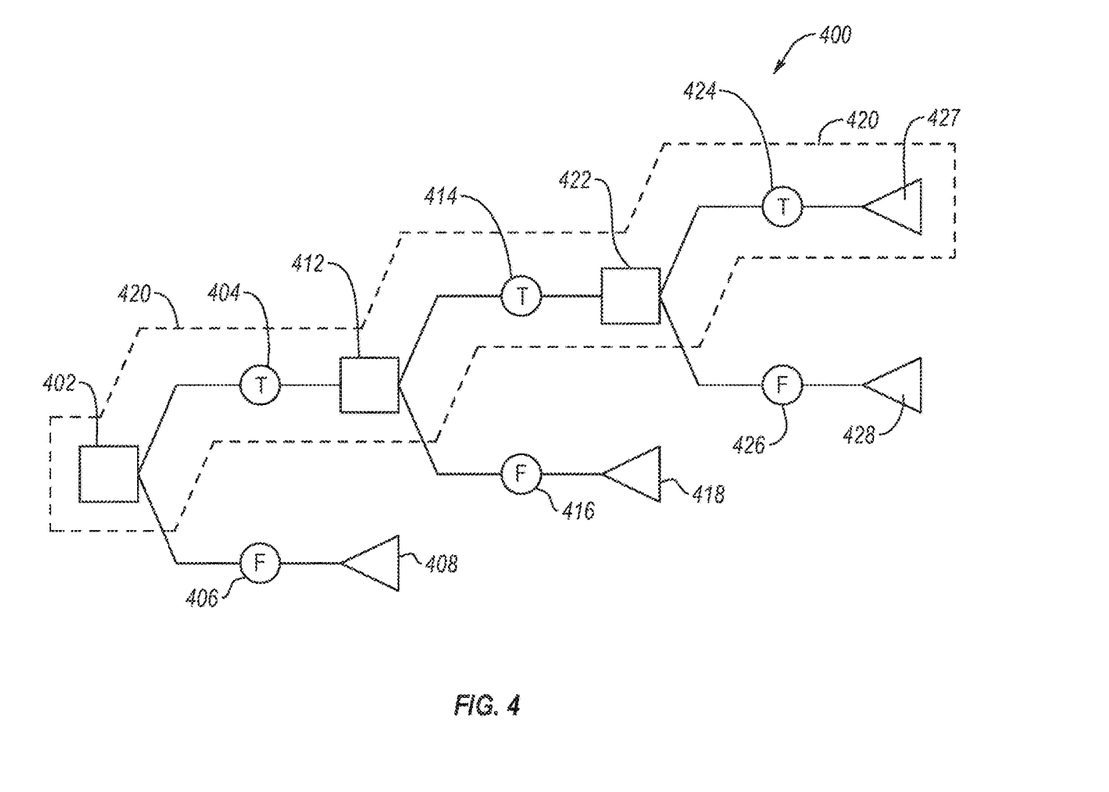
FIG. 4 is a schematic of a reasoning graph, according to an embodiment.

Reasoning graphs may be constructed to provide insights based on selected policies for use in the methods and systems disclosed herein. FIGS. 2-4 illustrate reasoning graphs, according to various embodiments. FIG. 2 is a reasoning graph 200 for determining if a request for a selected medication is appropriate, according to an embodiment. The reasoning graph 200 includes a plurality of reasoning functions 202 and 212. Each reasoning function 202 or 212 includes a query and at least two possible discrete decisions (e.g., outcomes at 204 or 206, or 214 or 216) made at the reasoning function(s) 202 or 212 by answering the respective query with the information contained in the uniquely identifiable data. Discrete decision 204 or 206 (e.g., outcome(s)) may lead to another reasoning function 212 or to an insight 208, 217, or 218. For example, the first reasoning function 202 may query as to whether a healthcare provider has submitted a claim for a specific medication. If no claim is submitted, then the discrete decision 206 is a no or false (F) and the reasoning path 220 advances to the insight 208. The insight 208 may include instructions that no action should be taken (e.g., claim should not be paid and/or no prescription should be provided). The reasoning path 220 later provided to an entity (e.g., healthcare provider, insured, or insurer) only includes the reasoning function 202 (e.g., query therein), the discrete decision 206, and the insight 208. Accordingly, substantially no uniquely identifiable data/information is disclosed, while simultaneously providing an explanation of the reasoning behind the insight final decision).

If a claim was submitted by the healthcare provider, then the query of reasoning function 202 is answered with the discrete decision 204 true (T) or yes and the reasoning path advances to reasoning function 212. At reasoning function 212, the query is whether or not a diagnosis consistent with the need for the requested mediation is indicated (e.g., in medical records or claim header) in the uniquely identifiable data. One of two discrete decisions can be made using the uniquely identifiable data and responsive to the query. An affirmative answer or true (T) value in the discrete decision 214 results in the insight 217, and a negative answer or false (F) value results in the insight 218. Insight 217, selected responsive to a true (T) value at 214, may include instructions to pay the claim, provide the prescription for the medication, or determine that proper administrative policies were followed. Insight 218, selected responsive to a false (F) value at discrete decision 216, may include instructions that no action should be taken (e.g., claim should not be paid and/or no prescription should be provided). In each instance, only the reasoning path to the insight may be divulged or disclosed, not the entire reasoning graph or any of the uniquely identifiable data used to determine the discrete decisions. Accordingly, only selected portions of the reasoning graph directly relevant to the insight may be divulged to an entity (e.g., insured, insurer, or medical provider). Each insight 208, 217, or 218 includes an insight ID, which encodes the reasoning path used to reach the insight 208, 217, or 218 therein. For example, the insight ID for the leaf node containing the insight 208 includes the reasoning path 220, and each of reasoning function 202 and discrete decision therein 206.

As noted above, different criteria or constraints may be used in different reasoning functions. For example, as shown above, some reasoning functions may be based on a binary, affirmative or negative decision to query. Some reasoning functions may be based on quantitative measures, such as amounts and thresholds or limits associated therewith. In contrast to a diagnosis constraint (e.g., affirmative or negative decisions) as explained with respect to FIG. 2, in some embodiments, a maximum or minimum value constraint may be used.

FIG. 3 is a reasoning graph 300 for determining if a request for a selected amount of medication is appropriate (e.g., a maximum or minimum units constraint), according to an embodiment. The reasoning graph 300 includes a plurality of reasoning functions 302 and 312. Each reasoning function 302 or 312 includes a query and at least two possible discrete decisions (304 or 306, or 314 or 316). The discrete decisions 304 or 306, or 314 or 316 may be made at the reasoning function(s) 302 or 312 by answering the respective query with the information present in the uniquely identifiable data. Discrete decisions 304 or 306 may lead to another reasoning function 312 or to an insight 308, 317, or 318. For example, the first reasoning function 302 may query as to whether a healthcare provider has submitted a claim for a specific medication. If a claim was submitted, then the discrete decision 306 is a yes or true (T) and the reasoning path 320 advances to the second reasoning function 312, If a claim was not submitted, then an alternative reasoning path (not shown) would advance to the insight 308. The insight 308 may include instructions that no action should be taken (e.g., claim should not be paid and/or no prescription should be provided).

Returning to the reasoning path 320, upon querying the uniquely identifiable data and determining that the claim for the medication was submitted, the reasoning path 320 advances to the second reasoning function 312. The second reasoning function 312 may query the amount of units of medication billed for a drug code corresponding to the prescribed medication on the date of service (e.g., just on the date of service or cumulatively, including the date of service and some timeframe extending therefrom). Further, the second reasoning function 312 may compare the amount of units of medication billed to some threshold amount (e.g., maximum or minimum allowable units). Responsive to the second reasoning function 312, a system operating the reasoning graph 300 may determine, with the uniquely identifiable data, if the number of units of medication billed for the drug code exceed or fall short of the threshold amount. The threshold amount can be set according to a policy as disclosed above (e.g., an FDA recommendation). If the number of units falls short of the threshold amount, then a negative or false (F) value is given for the discrete decision 316 and the reasoning path would advance to the insight 318. The insight 318 may provide that no action should be taken with respect to the number of units requested (e.g., claim may proceed as submitted or medication should be filled as submitted).

If the number of units exceeds the threshold value, then the discrete decision 314 includes an affirmative or true value (T). In some embodiments, the discrete decision corresponding to the reasoning function 312 may additionally or alternatively include the total number of units, the number of units exceeding the maximum threshold, or the number of units that the submission is under a minimum threshold). Responsive to the determination that the number of units submitted exceeds the threshold value, given by the discrete decision 314, the reasoning path 320 advances to the insight 317. The insight 317 may provide that the number of units be reduced to comply with the policy (e.g., FDA recommendation).

Only the reasoning path 320 to the insight 317 may be divulged, not the entire reasoning graph 300 or any of the uniquely identifiable data used to determine the discrete decisions. As shown, the reasoning path 320 later provided to an entity (e.g., healthcare provider, pharmacist, insured, or insurer) only includes the reasoning functions 302 and 312 (e.g., queries therein), the discrete decisions 304 and 314, and the insight 317. Accordingly, only selected portions of the reasoning graph 300 directly relevant to the insight 317 may be divulged to an entity (e.g., insured, insurer, or medical provider).

Each insight 308, 317, or 318 includes an insight ID, which encodes the reasoning path used to reach the insight 308, 317, or 318 therein. For example, the insight ID for the leaf node containing the insight 317 includes the reasoning path 320, and each reasoning function 302, 312 and discrete decision 304 and 314 therein. Substantially no uniquely identifiable data is disclosed. Each insight may include a textual explanation of the outcome of the insight and/or of each portion of the decision path corresponding thereto. For example, the insight 317 may include a textual explanation of each portion of the decision path 320, such as each reasoning function and discrete decision therein. The insight 317 may include a textual explanation of the outcome of the decision path, such as explaining that the submitted amount exceeded the amount allowed under the policy and that an adjustment in the amount is required to comply with the policy. In some embodiments, the insight (317) may also explain at least some of the policy. For example, the insight 317 may explain that the correction in the amount of medication requested was provided to comply with FDA guidelines (e.g., as provided on the FDA approved package insert) with respect to the corresponding medication. As noted above, the insights 308, 317, 318 each include a unique insight ID (which may be encoded in a UUID output to an entity).

In some embodiments, a waste constraint may be used, FIG. 4 is a reasoning graph 400 for determining if a request for a selected amount of medication is appropriate (e.g., would result in wasted medication), according to an embodiment. The reasoning to graph 400 includes a plurality of reasoning functions 402, 412, and 422. Each reasoning function 402, 412, and 422 includes a query and at least two possible discrete decisions (404 or 406, 414 or 416, or 444 or 426). The discrete decisions 404 or 406, 414 or 416, or 444 or 426 may be made at, or responsive to, the reasoning function(s) 402, 412, or 422 by answering the respective query with the information present in the uniquely identifiable data. Discrete decisions 404 or 406, 414 or 416, or 444 or 426 may lead to another reasoning function (412 or 422) or to an insight (408, 418, 427 or 428). For example, the first reasoning function 302 may query as to whether a healthcare provider has submitted a claim for a specific medication. If a claim was submitted, then the discrete decision 406 is a yes or true (T) and the reasoning path 420 advances to the second reasoning function 412. If a claim was not submitted then an alternative reasoning path (not shown) would advance to the insight 408. The insight 408 may include instructions that no action should be taken to advance the reasoning path (e.g., claim should not be paid and/or no prescription should be provided).

Returning to the reasoning path 420, upon querying the uniquely identifiable data and determining that the claim for the medication was submitted, the reasoning path 420 advances to the second reasoning function 412. The second reasoning function 412 may query if a selected medication was requested in conjunction with a complementary medication (e.g., a modifier). Responsive to the second reasoning function 412, a system processing the reasoning graph 400 may determine, with the uniquely identifiable data, if the medication was requested in conjunction with a complementary medication. If the medication was not requested in conjunction with a complementary medication, then a negative or false (F) value is given for the discrete decision 416 and the reasoning path would advance to the insight 418. The insight 418 may provide the conclusion that no action should be taken to alter the number of units requested (e.g., claim may proceed as submitted or medication should be filled as submitted). If the medication was requested in conjunction with a complementary medication, then a positive or true (I) value is given for the discrete decision 414 and the reasoning path 420 advances to the third reasoning function 422.

The third reasoning function 422 may query the amount (units) of medication (e.g., a drug code corresponding thereto) requested or billed in conjunction with the complementary medication. Further, the third reasoning function 422 may compare the amount of units of the medication billed to some threshold amount (e.g., maximum or minimum allowable units) corresponding to the simultaneous request for the complementary medication. For example, the complementary medication may reduce or increase a total number of allowable units (e.g., threshold amount) of medication under a policy. Responsive to the third reasoning function 422, a system processing the reasoning graph 400 may determine, with the uniquely identifiable data, if the number of units of medication billed for the drug code exceed or fall short of the threshold amount. The threshold amount can be set according to a policy as disclosed above (e.g., an FDA recommendation). If the number of units falls short of the threshold amount, then a negative or false (F) value is given for the discrete decision 426 and the reasoning path would advance to the insight 428. The insight 428 may provide that no action should be taken with respect to the number of units requested (e.g., claim may proceed as submitted or medication should be filled as submitted).

If the number of units exceeds the threshold value, then the discrete decision 424 includes an affirmative or true value (T). In some embodiments, the discrete decision corresponding to the reasoning function 422 may additionally or alternatively include the total number of units, the number of units exceeding the maximum threshold, or the number of units that the submission is under a minimum threshold. Responsive to the determination that the number of units submitted exceeds the threshold value, given by the discrete decision 424, the reasoning path 420 advances to the insight 427. The insight 427 may provide that the claim is denied, the medication should not be filled, or the number of units should be reduced to comply with the policy (e.g., FDA recommendation).

Only the reasoning path 420 to the insight 427 may be divulged, not the entire reasoning graph 400 or any of the uniquely identifiable data used to determine the discrete decisions. As shown, the reasoning path 420, later provided to an entity (e.g., healthcare provider, pharmacist, insured, or insurer), only includes the reasoning functions 402, 412, and 422 (e.g., queries therein); the discrete decisions 404, 414, and 424; and the insight 427. Accordingly, only selected portions of the reasoning graph 400 directly relevant to the insight 427 may be divulged to an entity (e.g., insured, insurer, or medical provider).

Each insight 408, 418, 427 and 428 includes an insight ID, which encodes the reasoning path used to reach the respective insight. For example, the insight ID for the leaf node containing the insight 427 includes the reasoning path 420, and each reasoning function 402, 412, and 422 and discrete decision 404, 414, and 424 therein. Because uniquely identifiable data from multiple individuals may travel along the same reasoning in path 420, substantially no uniquely identifiable data is provided in the reasoning path 420 or is disclosed by the dissemination thereof. Accordingly, disclosure of the insight, reasoning graph, reasoning path, reasoning functions, and discrete decisions do not disclose uniquely identifiable data that is attributable to any specific individual. Each insight may include a textual explanation of the outcome of the insight and/or of each portion of the decision path corresponding thereto. For example, the insight 427 may include a textual explanation of each portion of the decision path 420, such as each reasoning function and discrete decision therein. The respective insights may include a textual explanation of the outcome of the corresponding decision path. For example, the insight 427 may include a textual or audio explanation that the submitted amount of medication in conjunction with the complementary medication exceeded the amount of medication allowed under the policy and that the claim or order was therefore denied (e.g., an adjustment in the amount is required to comply with the policy). In some embodiments, the insight (427) may also explain at least some of the policy. For example, the insight 427 may explain that when the medication is prescribed in conjunction with (or taken simultaneously with) the complementary medication, a limit on the specific amount of the medication allowed under the policy is adjusted (downward) to comply with FDA guidelines. As noted above, the insights 408, 418, 427, and 428 each include a unique insight ID (which may be encoded in a UUID output to an entity).

Reasoning graphs 200, 300, and 400 in FIGS. 2-4 are examples and may represent simplified reasoning graphs. In some embodiments, reasoning graphs may include any number of reasoning functions, discrete decisions, and insights. While depicted as binary decisions, the reasoning graphs may not include solely binary decisions of reasoning functions. A reasoning function may include two or more discrete decisions or outcomes. For example, reasoning functions may include quantitative queries, which include two or more discrete decisions based on a quantity identified in the uniquely identifiable data. In some embodiments, the reasoning graphs are provided or built in computer readable and executable code and one or more computer systems may run the reasoning functions and queries, and provide the discrete decisions and insights. While healthcare related examples are provided as examples herein, in some embodiments, other types of reasoning functions and may be used with uniquely identifiable data. For example, financial related reasoning functions may be provided and used, such as a reasoning function for determining if an entity qualifies for a loan or rate, for determining when to foreclose on an asset, for determining when to move capital from or into a fund, etc, in such embodiments, the uniquely identifiable data may include personally identifiable financial information that may be regulated by privacy of consumer financial information rules.

Returning to FIG. 1, the method 100 includes the act 120 of responsive to determining the insight and with the computing device, providing a universally unique identifier (UUID) encoding the insight ID. A UUID may be generated (e.g., randomly) by a UUID generator and includes a 128 bit number that is not practicably duplicated by later-generated UUIDs. The UUID encodes the insight ID. That is, the UUID includes one or more numbers or codes that identify a specific insight ID. For example, a specific insight ID may be identified by a UUID that has been generated and correlated to the insight M. In such embodiments, each UUID generated for a specific insight ID may be characterized in a database or computer system as encoding or corresponding to the insight ID. Accordingly, the insight ID is encrypted within the UUID, thereby adding an additional layer of protection against unwanted disclosure of information relating to an insight. As the UUIDs are randomly generated, the insight IDs encrypted therein cannot be determined from a pattern in the UUID. Such additional layer of protection provides a double encryption of the information relating to the insight. First, the uniquely identifiable data is stored in an encrypted database that is not accessible aside from processing reasoning graphs with the uniquely identifiable data (e.g., no uniquely identifiable data in the encrypted database is publicly or privately accessible for viewing). Second, the insight ID is encrypted in the UUID and provides no information unless and until the same is entered into a portal having programming to correlated the UUID to the insight ID.

In some embodiments, providing a UUID encoding the insight identifier may include selectively sending the UUID to an electronic address corresponding to or associated with the unique entity, via electronic communication. An electronic address may include and e-mail address or a telephone number. The electronic communication may include an e-mail, a text message, or an audio message (e.g., a robo-call). The electronic communication may include the UUID and, optionally, a website URL identifier where a portal for entering the UUID may be accessed. For example, selectively sending the UUID to an electronic address corresponding to or associated with the unique entity may include generating and sending an e-mail communication including to the UUID therein. A computer system or server used to determine the insights) may include computer readable and executable programs stored therein having code to generate and/or send the electronic communication to the respective electronic address.

In some embodiments, selectively sending the UUID to an electronic address corresponding to or associated with the unique entity may include sending the UUID to one or more electronic addresses corresponding to one or more unique entities. The one or more unique entities can include one or more of a patient; an insured individual; a care taker; a guardian (e.g., parent); service provider such as a medical professional (e.g., a doctor, nurse, etc.); a pharmacist; an investigator; an accountant, etc.; an insurer, or any other person who may be associated with uniquely identifiable data and/or an insight based thereon.

In some embodiments, a reasoning graph may change according to changes in policies over time. In such embodiments, a version-specific reasoning graph may include a version-specific set of reasoning functions. Accordingly, each version-specific insight may be encoded by a corresponding version-specific insight ID at the respective leaf node. The version-specific insight ID corresponding to the version-specific reasoning graph may be encoded/encrypted in the UUID. For example, the UUID corresponding to an insight ID, such as version-specific insight ID, is randomly generated then correlated to the version-specific insight ID (e.g., within an encrypted database) and therefore is not susceptible to decryption or decoding to determine the underlying version-specific insight ID. In such embodiments, the exact set of version-specific reasoning functions used to determine the version-specific insight may be recalled or provided at a portal at a later date, regardless of the current set of reasoning functions and/or insights in the reasoning graph currently in use. Accordingly, entities may view the rationale or reasoning behind an insight determined with an outdated set of reasoning functions. Such version-specific reasoning graphs, functions, insight IDs, etc. may be stored with the hosting entity in the hosting entity's servers) for later reference.

The method 100 includes the act 130 of providing a portal associated with the insight identifier, the portal configured receive input of the UUID and to display each of the plurality of reasoning functions and discrete decisions from the reasoning path corresponding to the insight identifier encoded in the UUID. In some embodiments, the portal configured receive input of the UUID and to display each of the plurality of reasoning functions and discrete decisions from the reasoning path may be configured to display only the reasoning functions and discrete decisions from the decision path corresponding to the insight identifier encoded in the UUID.

In some embodiments, providing a portal associated with the insight identifier may include providing electronic access to textual explanations of an insight corresponding to an insight ID encoded in the UUID. Electronic access may include web-based access such as a web page having a portal therein that accepts entry of UUIDs, and responsive thereto, communicates (e.g., displays or audibly recites) one or more portions of the reasoning path associated with the UUID (via the insight ID encoded therein), including the insight. Electronic access may include an automated telephone system configured to accept alpha-numeric input (e.g., the UUID) and responsive thereto, provide audible communication of the textual explanation of the insight.

Textual explanations of an insight may include one or more of a recitation of at least one query, at least one discrete decision, and an insight. Textual explanations may include a script corresponding to the insight, where the script includes the result of the insight (e.g., coverage will not be provided, the proposed medical procedure does not fit the documented symptoms, a person is likely committing fraud). The textual explanation may be free of uniquely identifiable data. For example, the textual explanation may include substantially only a query (e.g., reasoning function) and an outcome (e.g., discrete decision) for each discrete portion of the reasoning path, both of which are free of uniquely identifiable data attributable to any unique entity. Accordingly, a computer system (e.g., server(s)) processing the reasoning graphs with the uniquely identifiable data may partition or separate the textual explanations from the reasoning graph (as a whole) and the uniquely identifiable data. Computer systems configured to process the reasoning graphs as disclosed herein represent an improvement to computational information security because the uniquely identifiable data is divorced from the textual explanations that are output to outside entities and even employees of the hosting entity. Further, the textual explanations themselves are secured by the use of UUIDs, which provide a code that is not practicably repeated by any known method, and that encodes the textual explanation corresponding to the insight ID.

The method 100 includes the act 140 of displaying, in the portal, each of the plurality of reasoning functions and the discrete decisions made using the uniquely identifiable data along the reasoning path corresponding to the insight ID, responsive to input of the UUID. In some embodiments, displaying, in the portal, each of the plurality of reasoning functions and discrete decisions made using the uniquely identifiable data along the reasoning path corresponding to the insight ID includes displaying a textual explanation of each of the plurality of reasoning functions and discrete decisions made along the reasoning path. In some embodiments, displaying, in the portal, each of the plurality of reasoning functions and discrete decisions made using the uniquely identifiable data along the reasoning path corresponding to the insight ID includes causing a computing or communication device linked to the computer system via the portal to display a textual explanation of each of the plurality of reasoning functions and discrete decisions made along the reasoning path. The computing device may include a remote computer accessing a portal provided by the hosting entity (e.g., a web-page configured to provide the textual explanations responsive to entry of the UUID). The remote computer may include the computer of an entity such as any of the entities disclosed herein (e.g., insured, insurer, services provider, etc.). In some embodiments, the remote computing device may be remote from the hosting entity.

Causing a computing or communication device linked to the computer system via the portal to display a textual explanation of each of the plurality of reasoning functions and discrete decisions made along the reasoning path may include providing one or more textual explanations that are free of uniquely identifiable data. Causing a computing or communication device linked to the computer system via the portal to display a textual explanation can include generating and sending computer readable and executable instructions (e.g., HTML code) to a server or the computing device in communication therewith. The computer readable and executable instructions may include computer code with instructions to display the textual explanation having one or more of the reasoning path, at least one of the reasoning functions in the reasoning path, or at least one of the discrete decisions in the reasoning path.

In some embodiments, displaying, in the portal, each of the plurality of reasoning functions and discrete decisions made using the uniquely identifiable data along the reasoning path corresponding to the UUID may include displaying a textual explanation of each of plurality of reasoning functions and discrete decisions made along the reasoning path corresponding to a version-specific reasoning graph. The version-specific reasoning graph and corresponding version-specific reasoning functions, discrete decisions, and/ or insights may include textual explanations that do not apply to current reasoning graphs and corresponding reasoning functions, discrete decisions, and/or insights. Accordingly, an entity that provides a UUID corresponding to a version-specific insight ID (and associated version-specific reasoning graph and components thereof) may view only the version-specific textual explanations (e.g., version-specific reasoning path and associated components). In some embodiments, displaying, in the portal, each of the plurality of reasoning functions and discrete decisions made using the uniquely identifiable data along the reasoning path corresponding to the UUID may include displaying a textual explanation of each of plurality of version-specific reasoning functions and discrete decisions made along the version-specific reasoning path corresponding to the version-specific reasoning graph. In some embodiments, displaying in the portal may include providing an audio recital of the insight and/or the reasoning path and the associated reasoning functions and discrete decisions.

In some embodiments, the method 100 may further include receiving uniquely identifiable data attributable to the unique entity as the uniquely identifiable data. Receiving uniquely identifiable data attributable to the unique entity as the uniquely identifiable data may be carried out at or with the computing device. For example, receiving uniquely identifiable data attributable to the unique entity as the uniquely identifiable data can include receiving the uniquely identifiable data as a plurality of data points. In some embodiments, receiving uniquely identifiable data attributable to the unique entity can include converting or processing the uniquely identifiable data into the uniquely identifiable data as a plurality of data points. In some embodiments, automatically determining the insight may include using the plurality of data points to make each of the plurality of discrete decisions, such as responsive to a query posed by a reasoning function. In such embodiments, using the plurality of data points to make each of the plurality of discrete decisions may include automatically searching a database storing the plurality of data points therein for uniquely identifiable data corresponding to the query.

In some embodiments, the method 100 may include storing the uniquely identifiable data and the plurality of data points in a database. For example, storing the uniquely identifiable data and the plurality of data points may be done in an asymmetrically encrypted database in the computing device (e.g., computing device, system, or network, provided by the hosting entity) having no publicly accessible private key. In some embodiments, the database may not be accessible except to input data (e.g., uniquely identifiable data, reasoning graphs or portions thereof, etc.), process one or more reasoning graphs with uniquely identifiable data associated with a selected unique entity, or provide a portal as disclosed herein. Accordingly, the output of the database may be limited to only textual explanations of insights and/or reasoning paths (or portions thereof).

In some embodiments, the hosting entity may provide a system for providing de-identified insight information. That is, a system for providing insights and explanations of one or more portions thereof (e.g., reasoning path) that eliminates the possibility of disclosing the uniquely identifiable data used to reach the insight. One, some, or each of the acts described herein may be performed by a computing device a general purpose computer or server(s) suitably programmed to perform the acts).

Figure 5:
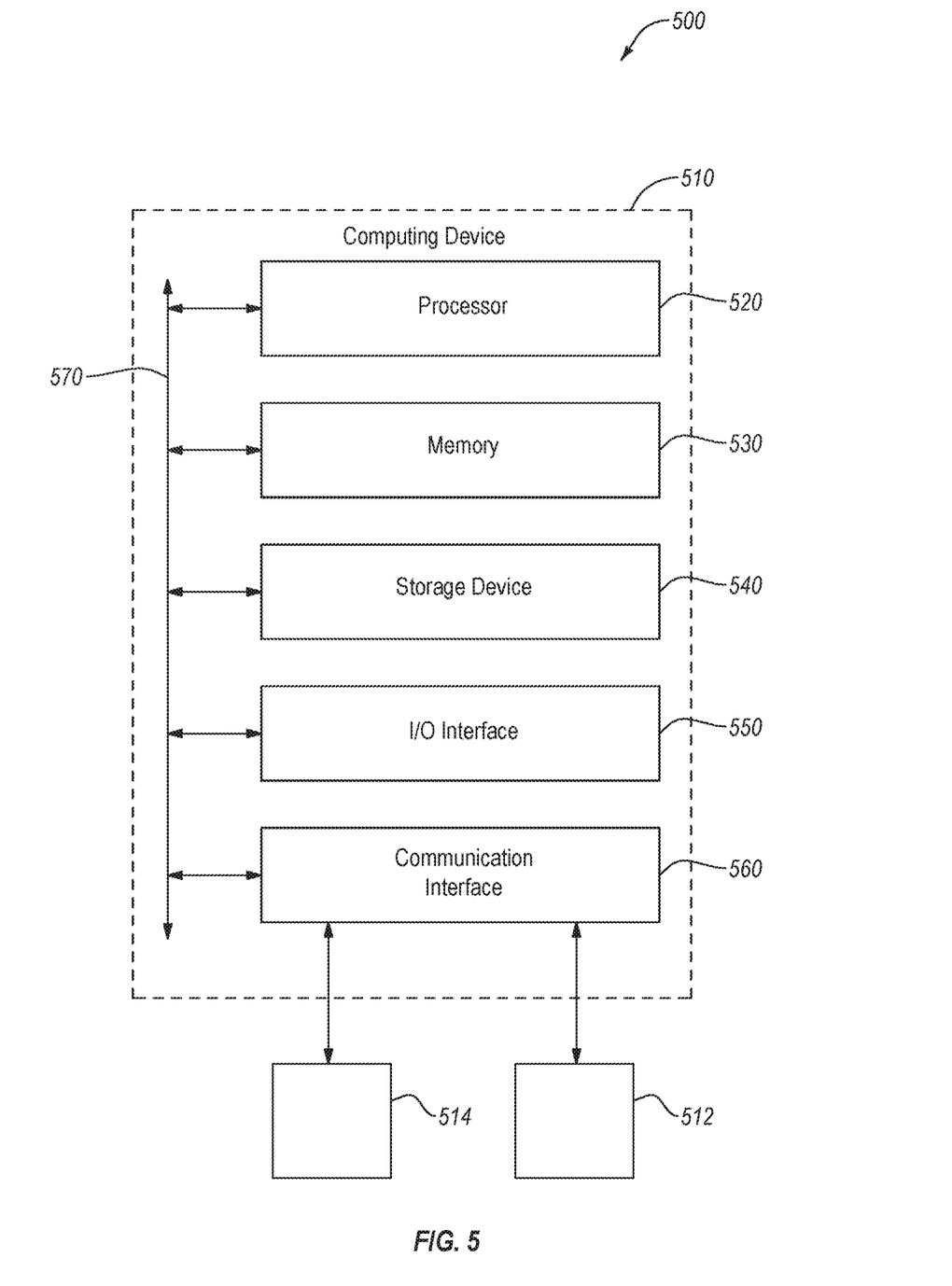
FIG. 5 is a schematic of a system for providing de-identified insight information, according to an embodiment.

FIG. 5 is a schematic of a system 500 for providing de-identified insight information, according to an embodiment. The system 500 may be configured to implement any of the methods disclosed herein, such as the method 100. The system 500 includes at least one computing device 510. In some embodiments, the system 500 may include one or more additional computing devices 512 and/or 514, such as operably coupled thereto over a network connection. The at least one computing device 510 is an exemplary computing device that may be configured to perform one or more of the acts described above, such as the method 100. The at least one computing device 510 can include one or more servers, one or more computers (e.g., desk-top computer, lap-top computer), or one or more mobile computing devices (e.g., smartphone, tablet, etc.). The computing device 510 can comprise at least one processor 520, memory 530, a storage device 540, an I/O interface 550, and a communication interface 560. While an exemplary computing device 510 is shown in FIG. 5, the components illustrated in FIG. 5 are not intended to be limiting of the system 500 or computing device 510. Additional or alternative components may be used in other embodiments. Further, in certain embodiments, the system 500 or the computing device 510 can include fewer components than those shown in FIG. 5. In some embodiments, the at least one computing device 510 may include a plurality of computing devices, such as a server farm, computational network, or cluster of computing devices. Components of computing device 510 shown in FIG. 5 are described in additional detail below.

In some embodiments, the processor(s) 520 includes hardware for executing instructions (e.g., processing a reasoning graph with selected uniquely identifiable data), such as those making up a computer program. For example, to execute instructions, the processor(s) 520 may retrieve fetch) the instructions from an internal register, an internal cache, the memory 530, or a storage device 540 and decode and execute them. In particular embodiments, processor(s) 520 may include one or more internal caches for data (e.g., uniquely identifiable data, reasoning graphs, correlation of a specific UUID or to insight ID to a specific reasoning graph, textual explanations corresponding to selected reasoning paths, etc.), instructions (e.g., operational program for processing a reasoning graph with selected uniquely identifiable data, operational programs for generating electronic communication of UUID to entities, operational programs for displaying or causing the display of textual explanations in the portal responsive to entry of a UUID), or addresses. As an example, the processor(s) 520 may include one or more instruction caches, one or more data caches, and one or more translation lookaside buffers (TLBs). Instructions in the instruction caches may be copies of instructions in memory 530 or storage 540. In some embodiments, the processor 520 may be configured (e.g., include programming stored thereon or executed thereby) to only output textual explanations of one or more of insights, reasoning paths, reasoning functions, discrete decisions, or outcomes corresponding to a UUID, such as via the portal.

In some embodiments, the processor 520 is configured to perform any of the acts disclosed herein such as in the method 100 or cause one or more portions of the computing device 510 or system 500 to perform at least one of the acts disclosed herein. Such configuration can include one or more operational programs that are executable by the at least one processor 520. For example, the processor 520 may be configured to automatically determine the insight using uniquely identifiable data attributable to the unique entity (e.g., uniquely identifiable data) and one the plurality of reasoning graphs. The at least one processor 520 may be configured to produce a UUID encoding the insight ID, such as a version-specific UUID. The at least one processor 520 may be configured to output the UUID, such as causing the I/O interface 550 to communicate the UUID to an entity via the communication interface 560. The at least one processor 520 may be configured to provide a portal associated with the insight ID, such as causing the I/O interface 550 to communicate a portal, for accessing and viewing a textual explanation corresponding to an insight ID (encoded in a UUID), to an entity via the communication interface 560 (e.g., provide a web-based portal). The at least one processor 520 may include programming to receive the UUID as input via the portal, such as from a remote computing device (e.g., additional computing device 514 operably coupled thereto, such as via a web-based or network connection. The at least one processor 520 may include programming to display, in the portal, the insight made using the uniquely identifiable data along the reasoning path corresponding to the insight ID, responsive to receiving the UUID. The at least one processor 520 may include programming to display, in the portal, each of the plurality of reasoning functions and the discrete decisions made using the uniquely identifiable data along the reasoning path corresponding to the insight ID, responsive to receiving the UUID. For example, the at least one processor 520 may cause the I/O interface 550 to communicate one or more of the insight, the plurality of reasoning functions, or the discrete decision(s) made using the uniquely identifiable data along the reasoning path corresponding to the insight ID (e.g., from a version-specific reasoning graph), to an entity via the communication interface 560.

The at least one computing device 510 (e.g., a server) may include at least one memory storage medium (e.g., memory 530 and/or storage 540). The computing device 510 may include memory 530, which is operably coupled to the processor(s) 520. The memory 530 may be used for storing data, metadata, and programs for execution by the processor(s) 520. The memory 530 may include one or more of volatile and non-volatile memories, such as Random Access Memory (RAM), Read Only Memory (ROM), a solid state disk (SSD), Flash, Phase Change Memory (PCM), or other types of data storage. The memory 530 may be internal or distributed memory.

The computing device 510 may include a storage device 540 having storage for storing data or instructions. The storage device 540 may be operably coupled to the at least one processor 520. In examples, the storage device 540 can comprise a non-transitory memory storage medium, such as any of those described above. The storage device 540 (e.g., non-transitory storage medium) may include a hard disk drive (HDD), a floppy disk drive, flash memory, an optical disc, a magneto-optical disc, magnetic tape, or a Universal Serial Bus (USB) drive or a combination of two or more of these. Storage device 540 may include removable or non-removable (or fixed) media. Storage device 540 may be internal or external to the computing device 510. In some embodiments, storage device 540 may include non-volatile, solid-state memory. In some embodiments, storage device 540 may include read-only memory (ROM). Where appropriate, this ROM may be mask programmed ROM, programmable ROM (PROM), erasable PROM (EPROM), electrically erasable PROM (EEPROM), electrically alterable ROM (EAROM), or flash memory or a combination of two or more of these. In some embodiments, one or more portions of the memory 530 and/or storage device 540 (e.g., memory storage medium(s)) may store one or more databases thereon. At least some of the databases may be asymmetrically encrypted. At least some of the databases that are asymmetrically encrypted may have no a publicly accessible private key. The at least some of the databases may be used to store uniquely identifiable data thereon, such as in data points. The at least some of the databases may be used to store one or more of a plurality of reasoning graphs (e.g., version-specific reasoning graphs), reasoning functions, insights, textual explanations, outcomes of reasoning graphs made using uniquely identifiable data, such as any of the above disclosed herein.

In some embodiments, uniquely identifiable data may be stored in a memory storage medium such as one or more of the at least one processor 520 (e.g., internal cache of the processor), memory 530, or the storage device 540. In some embodiments, the at least one processor 520 may be configured to access (e.g., via bus 570) the memory storage medium(s) such as one or more of the memory 530 or the storage device 540, For example, the at least one processor 520 may receive and store the uniquely identifiable data attributable to the unique entity as a plurality of data points in the memory storage medium(s). The at least one processor 520 may execute programming stored therein adapted access the uniquely identifiable data in the memory storage medium (s) to automatically determine the insight, such as using at least some of the plurality of data points to make the discrete decisions. For example, the at least one processor 520 may access one or more of uniquely identifiable data, reasoning graphs or portions thereof, or textual explanations stored in the memory storage medium(s) such as memory 530 or storage device 540. In some embodiments, the at least one processor 520 may include one or more operational programs therein that only output textual explanations of insights, reasoning paths, reasoning functions, discrete decisions, or outcomes, such as via the portal. Accordingly, the computing device 510 and the at least one processor 520 may provide a secure database for uniquely identifiable data, while only allowing output of insights, reasoning graphs, or portions thereof, each of which are substantially free of the uniquely identifiable data.

The computing device 510 also includes one or more input or output (I/O) devices/interfaces 550, which are provided to allow a user to provide input to, receive output from, and otherwise transfer data to and from the computing device 510. These I/O devices/interfaces 550 may include a mouse, keypad or a keyboard, a touch screen, camera, optical scanner, network interface, web-based access, modem, other known I/O devices or a combination of such I/O devices/interfaces 550. The touch screen may be activated with a stylus or a finger.

The I/O devices/interfaces 550 may include one or more devices for presenting output to a user, including, but not limited to, a graphics engine, a display (e.g., a display screen or monitor), one or more output drivers (e.g., display drivers), one or more audio speakers, and one or more audio drivers. In certain embodiments, devices/interfaces 550 are configured to provide graphical data (e.g., a portal and/or textual explanations) to a display (e.g., home or office computer screen) for presentation to a user. The graphical data may be representative of one or more graphical user interfaces and/or any other graphical content as may serve a particular implementation.

The computing device 510 can further include a communication interface 560. The communication interface 560 can include hardware, software, or both. The communication interface 560 can provide one or more interfaces for communication (such as, for example, packet-based communication) between the computing device 510 and one or more additional computing devices 512, 514 or one or more networks. For example, communication interface 560 may include a network interface controller (NIC) or network adapter for communicating with an Ethernet or other wire-based network or a wireless NIC (WNIC) or wireless adapter for communicating with a wireless network, such as a WI-FI.

Any suitable network and any suitable communication interface 560 may be used. For example, computing device 510 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, one or more portions of system 500 or computing device 510 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination thereof. Computing device 510 may include any suitable communication interface 560 for any of these networks, where appropriate.

In some embodiments, the computing device 510 may include a server having a network connection, and the server includes programming therein adapted to output the UUID over the network connection to an electronic address corresponding to an entity associated with the insight (e.g., a patient, a customer, a service provider, an insurer, an insured individual), responsive to determining the insight.

The computing device 510 may include a bus 570. The bus 570 can include hardware, software, or both that couples components of computing device 510 to each other. For example, bus 570 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination thereof.

It should be appreciated that any of the acts described herein, such as in the method 100, may be performed by and/or at the computing device 510. Additionally or alternatively, one or more of the acts described herein may be performed by or at another computing device such as additional computing device 512 or additional computing device 514. For example, some of the acts may be performed by or on a personal computing device of the user (e.g., additional computing device 512 or 514), such as a personal computer, smart phone, etc., (e.g., receiving electronic messages), while one or more of the acts may be performed by another computing device (e.g., computing device 510), such as a server, that may be operably connected to the personal computing device of the user (e.g., determination of an insight may be performed by a server that is connected to the computing device of the user via the Internet). Accordingly one or more elements of system 500 can be remotely distributed from one another distributed and/or one or more elements of the system 500 can be collocated. For example, entering uniquely identifiable data may be performed via the additional computing device 512, such as by a medical professional, an auditor, an accountant, etc., manually providing the uniquely identifiable data into the computing device 510 via a network connection, or, by automatically transferring uniquely identified data via a data transfer routine, order, dump, or other mechanism. In examples, the portal may be displayed on the additional computing device 514, such as via a web or network connection either directly or indirectly from the additional computing device 514 to the computing device 510.

In some embodiments, the at least computing device 510 (e.g., the server) may be operably coupled to at least one remote computing device (e.g., additional computing device 512 and/or 514) and includes one or more operational programs therein configured cause the portal to display, in the at least one remote computing device, a textual explanation of each of the plurality of reasoning functions and discrete decisions made along the reasoning path, responsive to receiving the UUID. For example, the at least one computing device 510 may include programming that includes an internet site stored therein that provides the portal. The programming for the internet site may include programming to provide an entry field for UUIDs and a display field for displaying textual explanations of one or more of reasoning graphs, insights, reasoning functions, discrete decisions, etc., corresponding to the insight ID encoded in the UUID. In some embodiments, the internet site may be an intranet site. One or more remote computing devices may have access to the internet site. Accordingly, the system 500 may include the first additional computing device 512. An entity or user may enter uniquely identifiable data or reasoning graphs (e.g., or any discrete portions thereof) into, and/or request an insight from, the computing device 510 via the first additional computing device 512.

Figure 6:
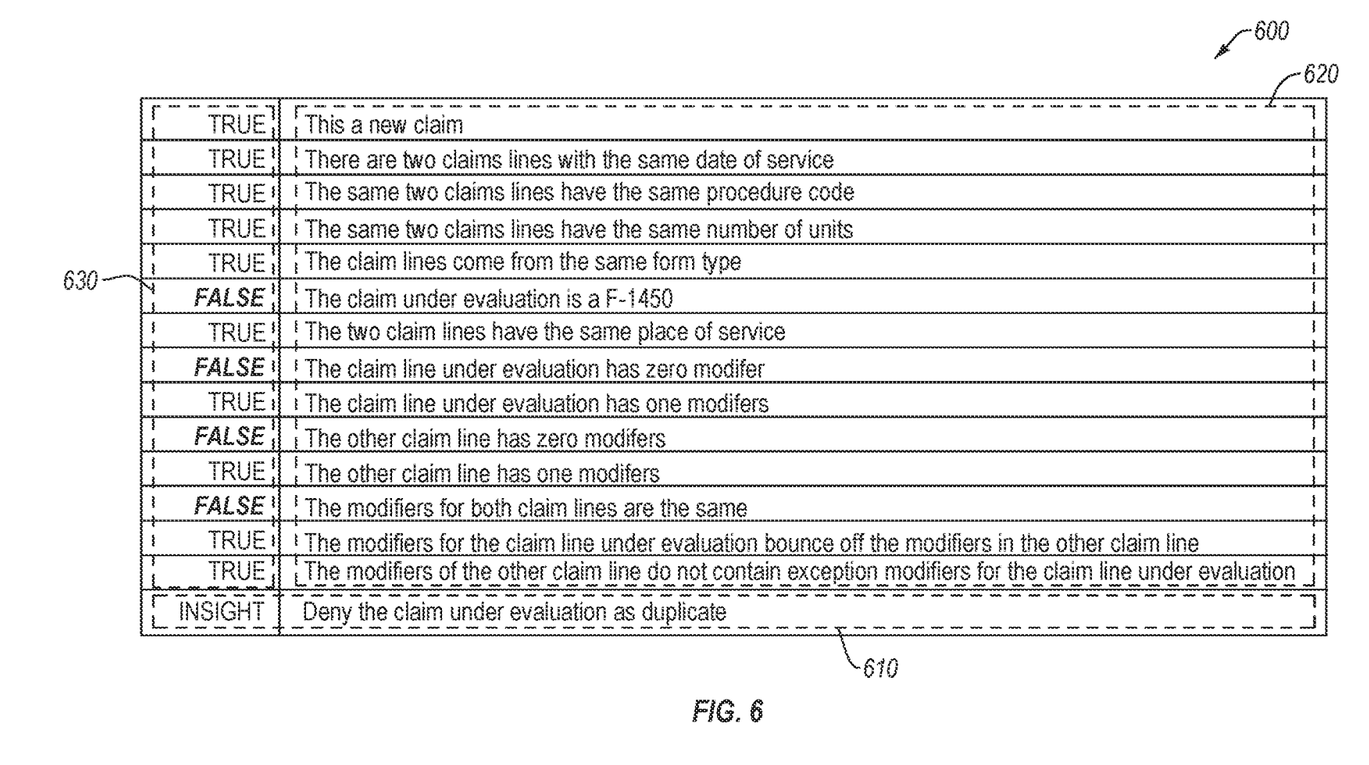
FIG. 6 is a view of a portal for viewing an insight according to an embodiment.

FIG. 6 is a portal 600 for viewing an insight generated by the systems and methods disclosed herein, according to an embodiment. The portal 600 may include one or more fields providing a textual explanation of an insight, reasoning function, or discrete decision, according to an embodiment. For example, the portal 600 may include a first field 610 for providing a textual explanation of the insight. The portal 600 may include one or more second fields 620 for providing a textual explanation of one or more reasoning functions in the reasoning path. The portal 600 may include one or more third fields 630 for providing a textual explanation of one or more discrete decisions, such as discrete decisions corresponding to the one or more reasoning functions in the second field 620.

As shown, the portal 600 allows a user or entity to view the reasoning behind an insight, without viewing any of the uniquely identifiable data used to arrive at the insight. In some embodiments (not shown), the portal 600 may include an entry box for entering a UUID. In some embodiments, the UUID may be entered on a different internet page than the portal 600.

Returning to FIG. 5, the system 500 may include additional computing device 514. Additional computing device 514 may include a computing device at a home or office of an entity. For example, the computing device 514 may include the desk-top computer of an employee of an entity, such as an insurer or service provider. The computing device 514 may be used to access the portal provided by the computing device 510, such as to input a UUID and view the textual explanations associated therewith. In some embodiments, the computing device 514 may include the desk-top computer of an insured individual and the computing device 510 may be located at the hosting entity, such as an insurance provider or services provider. The computing device 514 may be used to access the portal provided by the computing device 510, such as to input a UUID and view the textual explanations associated with healthcare related decisions applicable to the insured individual. The additional computing devices 512 or 514 may be similar or identical to the computing device 510 disclosed herein, such as having any of the components of the computing device 510 disclosed herein.

The systems and methods disclosed herein provide a number of improvements to current systems and methods for disclosing reasoning behind insights made with uniquely identifiable data. First, the systems and methods disclosed herein enable complete transparency of the logic or reasoning used to arrive at an insight—the reasoning path. For example, disclosure of the reasoning path enables a customer to explore each criterion used to arrive at the insight, thereby keeping the uniquely identifiable data on the customer side of said exploration. Second, all uniquely identifiable data used to arrive at or determine the insight is insulated from disclosure by storage in a non-accessible database (e.g., no uniquely identifiable data in the encrypted database is viewable by any entity including the hosting entity) and by providing only the reasoning path (e.g., reasoning functions, discrete decisions, and insight). Third, the reasoning paths and insights are encrypted by encoding the same in UUIDs that are not traceable to any specific uniquely identifiable data. Accordingly, the systems and methods herein provide improvements in handling of uniquely identifiable data, encryption of uniquely identifiable data and insights made using the same, processing of reasoning graphs using uniquely identifiable data to arrive at insights, and disclosure of reasoning behind insights and the logic used to arrive at the same.

While various aspects and embodiments have been disclosed herein, other aspects and embodiments are contemplated. The various aspects and embodiments disclosed herein are for purposes of illustration and are not intended to be limiting.

What is claimed is:

1. A method of producing insight reasoning about uniquely identifiable data over a computer network, the method comprising:
   with a computing device, producing one or more insights, each insight produced using at least a uniquely identifiable data attributable to a unique entity and a reasoning graph that incorporates one or more policies, the reasoning graph including:
      a plurality of leaf nodes each of which providing a candidate insight identifiable by an insight identifier that is encoded by a universally unique identifier (UUID),
      a plurality of reasoning paths each of which terminating in one of the plurality of leaf nodes, and
      a plurality of reasoning functions, each of the plurality of reasoning functions defining one or more criterion for making a discrete decision made with the uniquely identifiable data at a point along a reasoning path, at least some of the reasoning functions using the one or more policies to define the one or more criterion, the reasoning path to a specific insight defined at one of the plurality of leaf nodes by the insight identifier and not including the uniquely identifiable data; and
   sending, to a system over the computer network, one or more UUIDs for the one or more insights to avoid revealing the uniquely identifiable data over the computer network and to facilitate presentation, to a user at the system, of a final determination produced based on the one or more insights.

2. The method of claim 1, wherein the one or more insights are stored in a hosting entity or a server thereof.

3. The method of claim 1, wherein the system comprises a hosting entity that includes a data processing center that receives the one or more policies and information associated with the uniquely identifiable data, and determines the one or more insights with respect to the one or more policies using information associated with the uniquely identifiable data.

4. The method of claim 1, wherein the uniquely identifiable data includes personally identifiable information.

5. The method of claim 1, wherein the one or more policies includes one or more of: a government instruction, a recommendation by a governmental organization, a state statute or regulation, or a federal statute or regulation.

6. The method of claim 1, wherein the reasoning graph is implemented via machine readable and executable instructions that include queries formulated along the reasoning path to arrive at the specific insight.

7. The method of claim 1, comprising receiving the uniquely identifiable data attributable to the unique entity, at the computing device, as a plurality of data points.

8. The method of claim 7, wherein:
   producing the one or more insights includes using the plurality of data points to make each of the plurality of discrete decisions.

9. The method of claim 1, wherein the unique entity includes one or more of an insured individual or a medical professional associated therewith.

10. The method of claim 1, wherein the reasoning graph includes a directed acyclic graph.

11. The method of claim 1, wherein the one or more UUIDs correspond to a specific version of the reasoning graph.

12. The method of claim 11, further comprising causing the system receiving the one or more UUIDs encoding the one or more insights to recall a set of reasoning functions associated with the specific version of the reasoning graph based on the one or more UUIDs.

13. A system for providing de-identified insight information, the system comprising:
   an encrypted database storing uniquely identifiable data attributable to a unique entity and a plurality of reasoning graphs therein, each of the plurality of reasoning graphs comprising:
      a plurality of leaf nodes each of which providing a candidate insight identifiable by an insight identifier that is encoded by a UUID,
      a plurality of reasoning paths each of which terminating in one of the plurality of leaf nodes, and
      a plurality of reasoning functions, each of the plurality of reasoning functions defining one or more criterion for making a discrete decision made with the uniquely identifiable data at a point along a reasoning path, at least some of the reasoning functions using one or more policies to define the one or more criterion, the reasoning path to a specific insight defined at one of the plurality of leaf nodes by the insight identifier and not including the uniquely identifiable data; and
   at least one processor operably coupled to a non-transitory memory storage medium storing instructions that, when executed by the at least one processor, cause the system to implement operations comprising:
      automatically producing one or more insights, each insight produced using the uniquely identifiable data attributable to the unique entity and at least one of the reasoning graphs, and
      sending, to a remote system over a computer network, one or more UUIDs for the one or more insights to avoid revealing the uniquely identifiable data over the computer network and to facilitate presentation, to a user at the remote system, of a final determination produced based on the one or more insights.

14. The system of claim 13, wherein the operations further comprise storing the one or more insights at the encrypted database.

15. The system of claim 13, wherein the operations further comprise receiving the one or more policies and information associated with the uniquely identifiable data, and determining the one or more insights with respect to the one or more policies using information associated with the uniquely identifiable data.

16. The system of claim 13, wherein the uniquely identifiable data includes personally identifiable information.

17. The system of claim 13, wherein the reasoning graph is implemented via machine readable and executable instructions that include queries formulated along the reasoning path to arrive at the specific insight.

18. The system of claim 13, wherein the operations further comprise receiving the uniquely identifiable data attributable to the unique entity as a plurality of data points.

19. The system of claim 13, wherein the unique entity includes one or more of an insured individual or a medical professional associated therewith.

20. A system for providing de-identified insight information, the system comprising:
   a server including:
      at least one non-transitory memory storage medium having an encrypted database storing uniquely identifiable data attributable a unique entity and a plurality of reasoning graphs therein, each of the plurality of reasoning graphs comprising:
         a plurality of leaf nodes each of which providing a candidate insight identifiable by an insight identifier,
         a plurality of reasoning paths each of which terminating in one of the plurality of leaf nodes, and
         a plurality of reasoning functions, each of the plurality of reasoning functions defining one or more criterion for making a discrete decision made with the uniquely identifiable data at a point along a reasoning path, at least some of the reasoning functions using one or more policies to define the one or more criterion, the reasoning path to a specific insight defined at one of the plurality of leaf nodes by the insight identifier and not including the uniquely identifiable data, wherein the one or more policies includes one or more of: a government instruction, a recommendation by a governmental organization, a state statute or regulation, or a federal statute or regulation; and
      at least one processor operably coupled to the non-transitory memory storage medium, wherein the at least one processor is configured to:
         automatically produce one or more insights, each insight produced using at least one of the uniquely identifiable data attributable to the unique entity and at least one of the reasoning graphs, and
         based on the one or more insights, produce a final determination about a conclusion or propriety of a decision associated with the uniquely identifiable data, wherein the final determination is presentable to a user without revealing the uniquely identifiable data.

* * * * *

UNITED STATES PATENT AND TRADEMARK OFFICE
CERTIFICATE OF CORRECTION

PATENT NO. : 12,095,903 B2
APPLICATION NO. : 17/605559
DATED : September 17, 2024
INVENTOR(S) : Creel et al.

It is certified that error appears in the above-identified patent and that said Letters Patent is hereby corrected as shown below:

On the Title Page

In item (71), in Column 1, in "Applicant", Line 1, delete "COTIVITY CORPORATION," and insert -- COTIVITI, INC., --.

In item (71), in Column 1, in "Applicant", Lines 1-2, delete "Wilton, CT (US)" and insert -- Atlanta, GA (US) --.

In the Drawings

On sheet 1 of 6, in FIG. 1, and on the Title Page, the illustrative print figure, reference numeral 130, Line 4, delete "orresponding" and insert -- corresponding --.

In the Specification

In Column 2, Line 22, delete "nodes," and insert -- nodes. --.

In Column 5, Line 60, delete "selected to" and insert -- selected --.

In Column 8, Line 14, delete "final" and insert -- (e.g., final --.

In Column 9, Line 7, delete "312," and insert -- 312. --.

In Column 10, Line 23, delete "to graph" and insert -- graph --.

In Column 10, Line 63, delete "(I)" and insert -- (T) --.

In Column 11, Line 54, delete "in path" and insert -- path --.

Signed and Sealed this
First Day of April, 2025

Coke Morgan Stewart
*Acting Director of the United States Patent and Trademark Office*

CERTIFICATE OF CORRECTION (continued)
U.S. Pat. No. 12,095,903 B2

In Column 12, Line 52, delete "M. In" and insert -- ID. In --.

In Column 13, Lines 17-18, delete "including to" and insert -- including --.

In Column 13, Line 19, delete "insights)" and insert -- insight(s) --.

In Column 16, Line 23, delete "a" and insert -- (e.g., a --.

In Column 16, Line 64, delete "to insight" and insert -- insight --.

In Column 18, Line 46, delete "540," and insert -- 540. --.